United States Patent [19]

DeCamp

[11] Patent Number: 5,037,401

[45] Date of Patent: Aug. 6, 1991

[54] HYPODERMIC NEEDLE CANNULA GUARD

[76] Inventor: Dennis M. DeCamp, 4395 E. Lowell St., Ste. G, Ontario, Calif. 91761

[21] Appl. No.: 511,550

[22] Filed: Apr. 20, 1990

[51] Int. Cl.$^5$ ............................................. A61M 5/32
[52] U.S. Cl. ..................................... 604/192; 604/263
[58] Field of Search ...................... 604/192, 263, 187

[56] References Cited

U.S. PATENT DOCUMENTS

| | | |
|---|---|---|
| 2,110,123 | 3/1938 | Eisele . |
| 2,997,043 | 8/1961 | Flynn . |
| 3,537,452 | 3/1970 | Wilks . |
| 4,040,419 | 8/1977 | Goldman . |
| 4,643,722 | 2/1987 | Smith, Jr. . |
| 4,664,259 | 5/1987 | Landis . |
| 4,747,836 | 5/1988 | Luther . |
| 4,917,243 | 4/1990 | Abrams et al. ............... 604/263 X |

FOREIGN PATENT DOCUMENTS 8800477  1/1988  World Int. Prop. O. .......... 604/192

*Primary Examiner*—John D. Yasko
*Attorney, Agent, or Firm*—Harness, Dickey & Pierce

[57] ABSTRACT

A hypodermic needle cannula guard adapted to receive the cannula through an open slot and labyrinth passage into the interior of the guard or through a closed slit which the hypodermic needle cannula can enter through, the slit reclosing after passage of the cannula into the guard. The labyrinth passage inhibits exit of the cannula from the guard upon entry and the closed slit effectively encapsulates the cannula once it is entered into the guard. After entry of the cannula into the interior of the guard, the guard is pushed towards the hub of the hypodermic needle until the entry end of the guard and the hub of the needle are engaged and to secure the guard to the hypodermic needle.

8 Claims, 3 Drawing Sheets

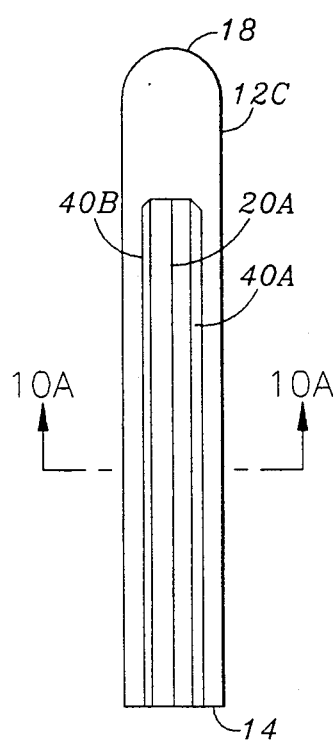
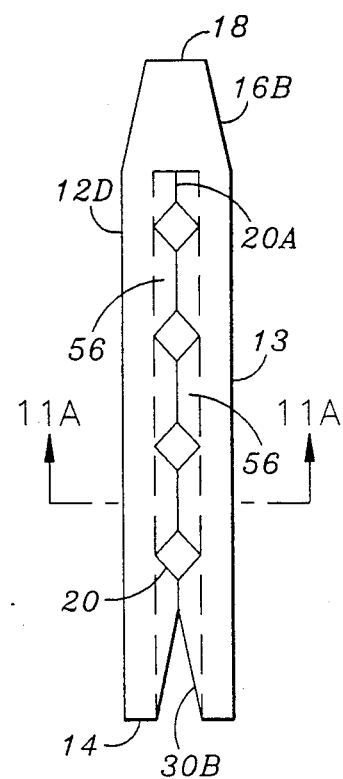
FIG. 10  FIG. 11
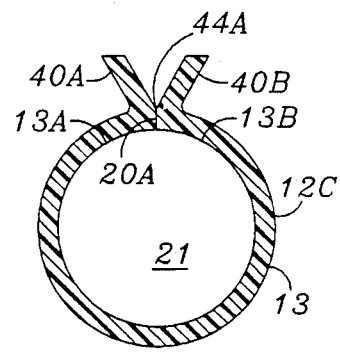
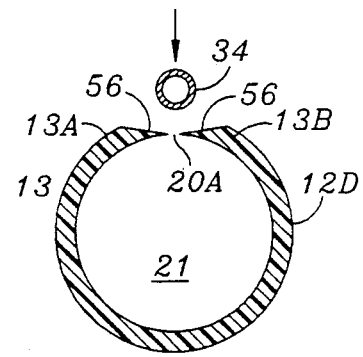
FIG. 10A  FIG. 11A

HYPODERMIC NEEDLE CANNULA GUARD

BACKGROUND OF THE INVENTION

1. Field of the Invention

This invention relates to hypodermic needle safety shields or enclosures, more particularly, a shield or enclosure that will receive a hypodermic needle cannula after use to safely enclose the cannula for disposal and prevent accidental puncture wounds.

2. Description of the Prior Art

Hypodermic needle cannula covers and safety shields have been known for some time. The interest in such devices has increased dramatically since the onset of AIDS and the recognition of the serious health problems associated with hepatitis. Both these illnesses are virus propagated. The virus can be readily transferred to a human through contaminated blood. A used hypodermic needle cannula contaiminated with AIDS or hepatitis infected blood can, by accidental puncture, cause the transfer of AIDS or hepatitis to a healthy or uninfected human.

U.S. Pat. No. 2,110,123 is directed to a hypodermic needle guard to prevent injury to the cannula tip during shipping, handling, sterilization, and the like. U.S. Pat. No. 2,997,043 discloses a protective sheath for a cannula which is used to protect the cannula prior to use. U.S. Pat. No. 3,537,452 discloses a needle cover and bevel guard which is designed to protect catheter tubes which are inserted into the body via a hypodermic needle cannula after removal of the cannula to prevent the cannula point from accidentally severing or puncturing the catheter tube. U.S. Pat. No. 4,643,722 discloses a guard for storage, transportation and disposal of hypodermic needles to prevent accidental puncture wounds following use of the needle. The guard is a tubular element having a longitudinal axial slot to permit entry of the cannula into the guard. To prevent exit of the needle from the guard, the guard is furnished with a removable sealing strip. U.S. Pat. No. 4,664,259 is directed to a hinged container enclosing a hypodermic needle cannula which is directly attached to the hub of a cannula. The container can be rotated away from the cannula with the cannula exiting through a slot in one wall of the container. In an alternative embodiment, the container has two wall segments hinged on opposite sides of the cannula which can be rotated away on their hinges to free the cannula for use. U.S. Pat. No. 4,747,836 discloses a cannula guard which is rotatably mounted at the base of the cannula and constitutes a half channel which receives the cannula. The cannula guard is rotated away from the cannula for use. The guard is rotated back to partially enclose the cannula after use and a cylinder is moved over the guard to enclose the cannula and the guard.

Although these cannula guards and enclosures are superior to the conventional cap-type enclosures which require that the used cannula point be centered into the open end of the cap and then projected into the cap during encapsulation. Medical workers, frequently during times of stress or fatigue, do not pay adequate attention to the cannula during the encapsulation process and accidentally puncture their hand or finger with the used cannula. Such accidental punctures have led to cases of hepatitis and AIDS, serious, life-threatening diseases.

The guard of U.S. Pat. No. 2,979,043 can only be used to protect a cannula before use. The metal guard of the U.S. Pat. No. 2,110,123 patent does not fully encapsulate the needle. The guard of the U.S. Pat. No. 3,537,452 patent is designed to be utilized with a catheter tube and, in the absence of a catheter tube, the cannula can exit via the elongated slot. The needle guard of the U.S. Pat. No. 4,643,722 patent has an open slot which, when not sealed, permits exit of the cannula. The slot can be fitted with a removable sealing strip, which can be used to cover the slot after entry of the cannula. However, a strip is inconvenient. The medical worker must place the sealing strip in a convenient location for retrieval after use of the cannula and must be careful when applying the sealing strip that the point of the cannula does not exit the slot and accidentally puncture the worker. In another embodiment, the sealing strip can be permanently attached to one end or side of the slot so that it is not separated from the guard. However, for this embodiment, the sealing strip must be held out away from the slot when the cannula is inserted into the guard. This can be a cumbersome process and, once again, expose the fingers or the hand to an accidental puncture wound. The needle container of the U.S. Pat. No. 4,664,259 patent is somewhat awkward and complicated and limits the area of access for the hypodermic needle because of the position of the open container. Similarly, the needle guard of the U.S. Pat. No. 4,747,836 patent is awkward to use because the needle guard is rotatably mounted to the base of the needle and can limit the area of access because of the physical incursion of the guard. The hypodermic needle guards of the U.S. Pat. Nos. 4,664,259 and 4,747,836 devices are relatively complex devices and much more costly than the hypodermic needle guards of the earlier patents.

The object of the present invention is to provide a needle guard which can easily receive the cannula of a hypodermic needle with minimum exposure to the user's fingers and hands to prevent accidental puncture wounds. In addition, it is an object of the present invention to provide a needle guard which encapsulates the cannula of a hypodermic needle to prevent or inhibit the exit of the cannula from the guard. Furthermore, it is an object of the present invention to provide a needle guard which can be manufactured from inexpensive materials, which comprises a relatively simple design which can be easily molded and which can be readily manufactured to provide a hypodermic needle guard at minimum cost.

SUMMARY OF THE INVENTION

The above objects have been met by the needle guard of the present invention which can be manufactured from polyethylene, polyprophylene or other inexpensive plastics and polymers to minimize the material cost. The guard is of a relatively simple design which makes the guard easy to mold, thus, minimizing the manufacturing costs of the guard. A cannula can be easily inserted into the guard and the guard safely encapsulates and imprisons the cannula to prevent escape.

Cannula guard for hypodermic needles of the present invention comprises an elongated hollow shell or tube having an interior wall, an exterior wall, an open receiver end and an opposing distal end, the shell having a central chamber bounded by the interior wall extending the length of the shell from the open receiver end, the central chamber divided into a first zone extending from the open receiver end toward the opposing end which is adapted to receive and secure the hub of a hypodermic needle cannula and a second zone extending from the first zone to the opposing distal end which is adapted to receive and enclose a hypodermic needle, the shell having an open slot running the length thereof from the open receiver end towards the opposing distal end, the slot forming a passage from the exterior of the shell into the central chamber; and screening means to screen the slot from the central chamber to form a labyrinth passage between the slot and central chamber to inhibit the chance of exit of a hypodermic needle cannula from the central chamber through the slot.

The screening means can be a screen wall in the second zone of the central chamber extending from the interior wall radially inwardly and circumferentially. The screen wall can be a wall extending from the interior wall on one side of the slot that circumferentially crosses or bridges the path of the slot. The far edge of the screening wall can contact the interior wall on the other side of the slot, sealing the slot from the central chamber. The screening wall is preferably a flexible wall that can bend inwardly when pressed by a cannula from the exterior to from an opening between the interior wall and face edge of the screen wall to permit entry of the cannula into the central chamber. Preferably, the screening wall is biased to close the opening after entry of the cannula. The distal end of the shell can be closed in, such as by a planar wall or a bullet-head wall. The slot extending into the central chamber in the first zone can be an enlarged slot having parallel walls or converging walls to aid in the positioning and entry of the cannula into the slot. The exterior wall can have a V groove which leads into the slot to help guide the cannula. As an alternative embodiment of the present invention, the shell can be fitted with radially, outwardly extending guide walls which form a V groove with interior wall surfaces extending or continuing into the walls of the slot to aid in the positioning and entry of the cannula into the slot. In one of the preferred embodiments of the present invention, the screen wall has a L-shaped cross section.

In a further embodiment of the present invention, the slot walls extend towards each other and come into contact therein to form a slit. The walls of the shell adjacent the slit are resilient or flexible so that the cannula can be inserted into the slit, forcing the slot walls to separate and open the slit to form the slot to permit passage of the cannula into the central chamber. Once the cannula has passed through the slot, the slot walls, biased towards one another, come together to collapse the slot and form the slit. The walls of the shell on either side of the slit can be formed into flexible wings that extend circumferentially towards each other or that extend radially inwardly toward each other at an angle to make contact and form the slit. Preferably, the cross-sectional thickness of the wings progressively decreases from the wall to the edge of the wings where the slit is situated. This design permits the wings to be flexible, allowing the cannula to be pressed down against the wings, forcing the wings to bend or flex away from the slit to form an open slot to permit the cannula to pass through the slot into the central chamber. The wings are biased to return to their original position after passage of the cannula, closing the slot to form the slit and sealing the cannula in the central chamber.

In still another embodiment of the present invention, the wall of the shell on one side of the slit extends radially outwardly to form one side of a V groove and the wall of the shell on the other side of the slit extends circumferentially inwardly toward the interior surface of the first wall to come in contact therewith to form a collapsed slot; the interior surface of the first wall in contact with the exterior surface of the second wall.

The cannula of the hypodermic needle is easily inserted into the cannula guard of the present invention by holding the guard between the thumb and two or more opposing fingers of one hand with the slot, groove or slit facing away from the hand. The hypodermic needle is held in the other hand and the cannula is positioned so that a portion of the cannula between its hub or base and its distal end is received in the opening of the slot or the groove or the slit near the open receiver end of the shell. The cannula is moved downwardly into the slot, groove or slit to extend the rest of the cannula from mid-portion to the point through the slot or groove, or slit into the central chamber. When the distal end of the cannula has entered the central chamber, the guard and the cannula are roughly coaxial and the cannula is moved inwardly into the central chamber towards the opposite distal end until the hub of the hypodermic needle has been received and secured in the first zone of the central chamber.

When the screen wall has a L-shaped cross-section, the cannula is inserted into the slot down to the bottom side or foot of the L-shaped screen wall and then the cannula is moved laterally away from the side or leg of the L-shaped screen wall into the central chamber. The cannula is then moved inwardly towards the opposite distal end of the central chamber until the hub of the hypodermic needle cannula is secured in the first zone.

BRIEF DESCRIPTION OF THE DRAWINGS

FIG. 10 is a top view of an alternative embodiment of the cannula guard of the present invention.

FIG. 10A is a cross-sectional view of an alternative embodiment of the cannula guard of the present invention;

FIG. 11 is a cross-sectional view of an alternative embodiment of the cannula guard of the present invention;

DESCRIPTION OF THE PREFERRED EMBODIMENT

Figure 1:
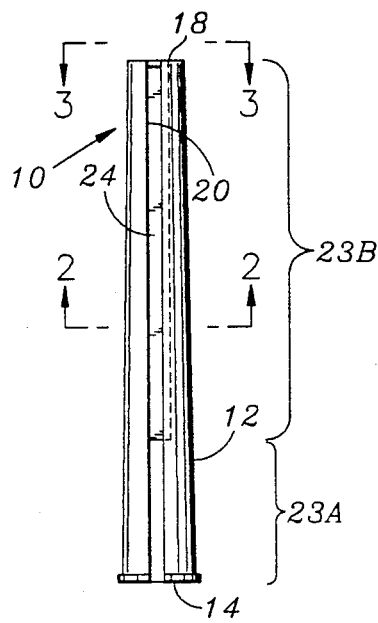
FIG. 1 is a top view of the hypodermic needle cannula guard of the present invention.
Figure 2:
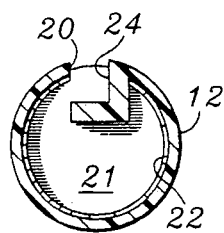
FIG. 2 is a cross-sectional view of the cannula guard of the present invention taken along lines 2—2 of FIG. 1.
Figure 3:
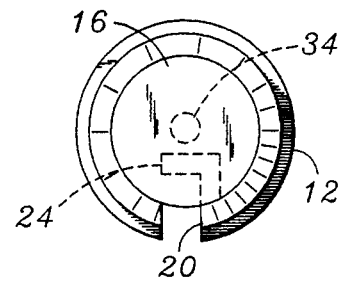
FIG. 3 is an end view of the cannula guard of the present invention taken along lines 3—3 of FIG. 1.

Referring to FIGS. 1–3, the cannula guard 10 of the present invention comprises a shell or tube 12 having an open receiver end 14 and a closed distal end 18 fitted with a planar wall 16 (See FIG. 3). A slot 20 extends from the open receiver end down the entire length of the shell and is adapted to receive the cannula of a hypodermic needle. The guard has a central chamber 21 divided into a first zone 23A and a second zone 23B. Extending radially inwardly and circumferentially from the inner surface 22 of the central chamber is a screen wall 24 adjacent one side of the slot. The screen wall substantially shields most of the central chamber from the slot and forms one side of a labyrinth passageway 25 for passage of a hypodermic needle cannula (not shown) from the slot 20 into the central chamber. The screen wall does not extend longitudinally into the first zone 23A of the central chamber. The first zone is clear of all obstacles that would interfere with receipt of the hub of the hypodermic needle cannula into the first zone. The interior surface 22 of the shell in the first zone is adapted to receive and secure the hub of a hypodermic needle cannula. The hub can be secured by a friction fit or protrusions extending inwardly from wall 22. The screen wall 24 does not have to extend the entire length of the second zone although it is preferred to have the screening wall cover the area of the central chamber wherein the distal end or tip or point of the cannula will reside when the guard and cannula have been secured to one another. The screen wall can be a continuous wall or an intermediate wall. Preferably, the end of the guard will have a wall, such as planar wall 16. However, the end can be open if the space between the distal end of the cannula and the distal end of the guard are sufficiently distanced to prevent the cannula point from tearing or puncturing skin that may come in contact with the distal end of the guard. The slot 20 does not have to extend the full length of the guard. The slot only has to be long enough to receive a portion of cannula for initial entry into the central chamber.

Figure 4:
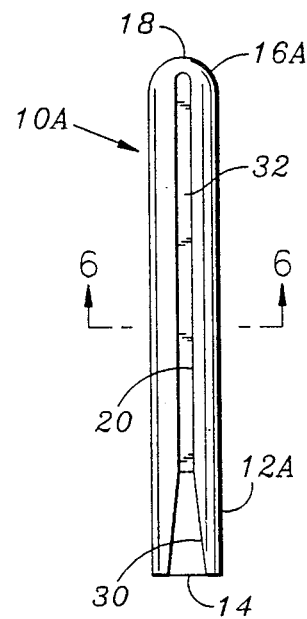
FIG. 4 is the top view of an alternative cannula guard of the present invention.
Figure 5:
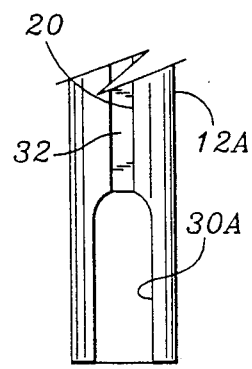
FIG. 5 is a partial top view of an alternative embodiment of the cannula guard of FIG. 4.

Referring to FIG. 4, an alternative embodiment of the cannula guard 10A of the present invention is illustrated. The cannula guard 10A has a shell or tube 12A having an open receiver end 14 and an opposing distal end 18 with a bullet nose enclosure wall 16A. The guard has an elongated slot 20 running a substantial length of the guard. At the open receiver end of the guard, the slot is formed into a V-shaped entry. The walls of the V-shaped entry diverge outwardly from the parallel wall portion 29 of the slot to the open receiver end. The V-shaped entry 30 aids in the positioning and entry of a cannula (not shown) into the slot 20. Other shaped entry slots can also be utilized. For example, in FIG. 5, there is shown an alternative entry slot 30A that has parallel walls which curve in to meet the walls of slot 20. Entry slot 30A also aids in the positioning and entry of a cannula (not shown) into the guard.

Figure 6:
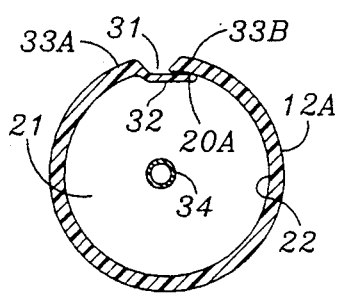
FIG. 6 is a cross-sectional view of the cannula guard of FIG. 4 taken along lines 6—6.
Figure 7:
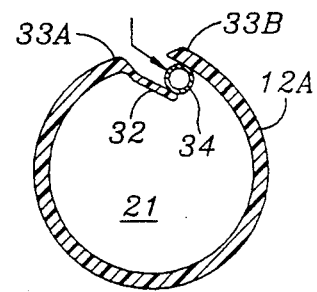
FIG. 7 is a cross-sectional view of the cannula guard of FIG. 6 showing the insertion of a hypodermic needle cannula into the guard.

Referring to FIGS. 6 and 7, slot 20 has a groove 31 terminating in a collapsed slot 20A created by flexible flap or trap door 32 extending radially inwardly and circumferentially from the interior surface 22 of wall 33A. Trap door 32 extends across the groove 31 and contacts the interior surface 22 of wall 33B on the opposite side of the groove to form collapsed slot 20A. The cannula 34 is positioned into groove 31 and moved radially inwardly to flex trap door 32 inwardly to open collapsed slot 20A and permit the passage of the cannula 34 into the central chamber 21. After passage of the cannula through the now opened slot 20A, the biased trap door moves back to its orginal position to collapse slot 20A and make contact with the interior side 22 of the opposing wall 33B.

Figure 8:
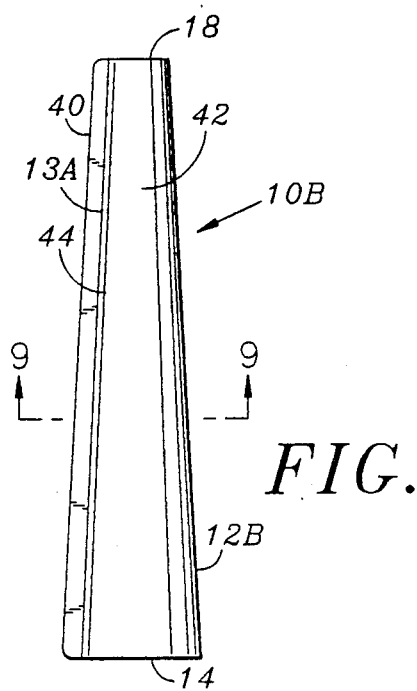
FIG. 8 is a top view of another alternative embodiment of the cannula guard of the present invention.
Figure 9:
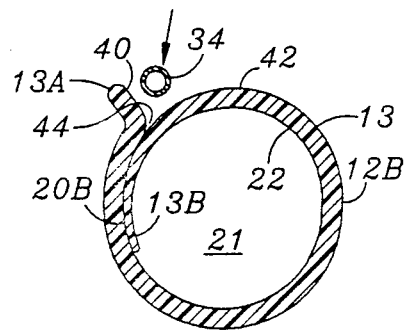
FIG. 9 is a cross-sectional view of FIG. 8 taken along section 9—9.

The hypodermic needle cannula guard 10B of FIGS. 8 and 9 comprises a shell 12B which is a section of a conical element and has an open receiver end 14 and an open opposing distal end 18. The wall 13 of the shell is rolled into a partial roll with 13A of the wall overlapping the other edge 13B of the wall. The first edge 13A of the wall forms a first side 40 of a groove 44 and a portion of the exterior surface of the other end 13B of the wall forms the other side 42 of the groove 44. The interior surface 22 of the edge 13A of the wall and the exterior surface of the other edge 13B of the wall are in contact to form a collapsed slot 20B. The first end 13A and the second end 13B are biased towards one another. The cannula 34 of the hypodermic needle can be inserted into the groove 34 and moved downwardly to force the sides 40 and 42 of the groove 44 apart and to open the collapsed slot 20A to permit passage of the cannula into the central chamber 21. After the cannula has passed into the central chamber, the biased ends 13A and 13B return to their original positions, collapsing the slot and effectively sealing the cannula into the central chamber 21. In the preferred embodiment, either one or both of the ends 13A or 13B will have a reduced thickness to enhance the flexibility of the sides of the groove.

FIG. 10 illustrates another embodiment of the cannula guard of the present invention wherein the cannula guard has an elongated collapsed slot 20A formed by the ends or edges 13A and 13B of the wall 13 of shell 12C. Extending radially outwardly from the exterior side of the wall 13 from the ends 13A and 13B are guide walls 40A and 40B which form a V-shaped groove 44A. The cannula (not shown) is positioned in the groove 44 and pushed or moved downwardly into the groove to force apart ends 13A and 13B and open collapsed slot 20A to permit the passage of the cannula into the central chamber 21. After the passage of the cannula, the biased ends 13A and 13B return to their original position, collapsing slot 20A and effectively sealing in the cannula in the central chamber 21.

FIGS. 11 and 11A show an alternative embodiment of the cannula guard of FIGS. 10 and 10A wherein the collapsed slot 20A of shell 12D is created by wings 56 extending circumferentially from the ends 13A and 13B of wall 13 of shell 12D. The shell has a conical section wall 16B at its distal end 18 and a curved open entry slot 30B at its open receiver end 14. The entry slot terminates into the collapsed slot 20A. Wings 56 wedged downwardly in thickness towards the collapsed slot 20A to increase the flexibility of the wings. The wings flex downwardly to open slot 20A to permit passage of cannula 34 when the cannula 34 is pressed against the wings in the vicinity of the collapsed slot 20A. After passage of the cannula 34 through the now open slot 20A into the central chamber 21, the wings which are biased, return to their previous position, collapsing the slot and effectively sealing the cannula in the central chamber 21. The wings are discontinuous and open slots 20 separate each set of wings. The wings can be continuous and the open slots 20 deleted.

Figure 12:
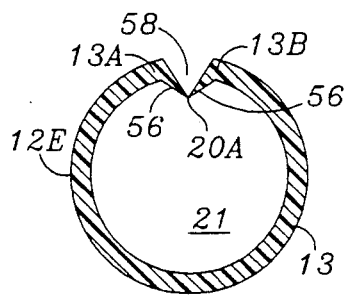
FIG. 12 is a cross-sectional view of an alternative embodiment of the cannula guard of the present invention.

FIG. 12 shows an alternative embodiment of the cannula guard of FIGS. 10, 10A and 11 and 11A wherein the ends 13A and 13B of wall 13 have wings 56 extending radially inwardly at an angle to form a V-groove 58. The ends of the wings 56 meet at a collapsed slot 20A. The wings wedge downwardly in thickness towards the slot 20A to increase the flexibility of the wings. When a cannula (not shown) is situated in V-groove 58 and pushed down against the wings towards the central chamber, wings 56 bend downwardly, opening the collapsed slot 20A, thus permitting the cannula to pass into the central chamber. After passage of the cannula, the wings which are biased towards each other return to their original position to close the slot 20A and effectively seal the cannula in the central chamber. The wings can be discontinuous as the wings of FIG. 11 or continuous.

Figure 13:
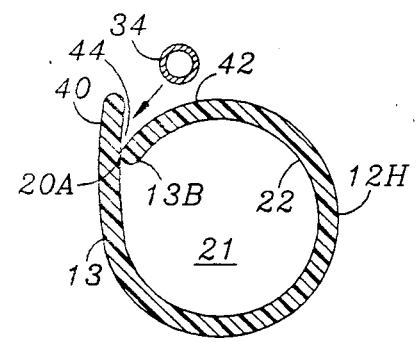
FIG. 13 is a cross-sectional view of an alternative embodiment of the cannula guard of the present invention.

FIG. 13 shows an alternative embodiment of the cannula guard of FIG. 9. The shell 12H of the cannula guard has the same elements as the cannula guard of FIG. 9 except that the end 13B of the wall 13 makes contact with the interior side 22 of the end 13A of the wall 13 to form groove 44. Cannula 34 is positioned in the groove 44 and pushed downward into the groove, causing end 13A of the wall 13 to separate from the end 13B of the wall, opening the collapsed slot 20A to permit the passage of the cannula into the central chamber. After the passage of the cannula through the now open slot, the biased ends 13A and 13B of the wall spring back towards each other to collapse slot 20A and effectively seal the cannula in the central chamber.

Figure 14:
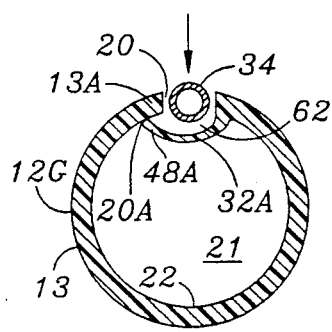
FIG. 14 is a cross-sectional view of an alternative embodiment of the cannula guard of the present invention.

Referring to FIG. 14, an alternative embodiment of the cannula guard of FIGS. 4-7 is shown wherein the slot 20 and the trap door 32A form a deep channel 62 which can receive the cannula 34. Flexible trap door 32A bends radially inwardly toward central chamber 21 when the cannula 34 is forced against the trap door to open collapsed slot 20A to permit the passage of the cannula into the central chamber. After the cannula has passed into the central chamber, the trap door 32A, which is biased, returns to its original position, thus effectively sealing the cannula into the central chamber 21.

Figure 15:
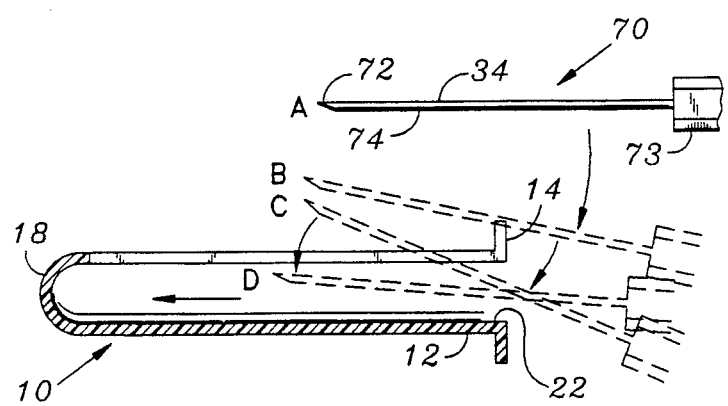
FIG. 15 is a cross-sectional side view of a cannula guard illustrating the insertion of a hypodermic needle cannula into the cannula guard of the present invention.

The method of positioning the hypodermic needle cannula into the cannula guard is illustrated in FIG. 15. A portion of the cannula 34 of the hypodermic needle 70 is positioned in the groove or slot of the cannula guard 10 and pushed downwardly through the slot or through the collapsed slot at the bottom of the groove into the central chamber as shown in steps A, B, C and D sequentially. Once the distal end or tip of the cannula 72 is positioned in the central chamber and the shaft 74 of the cannula has cleared the slot, the cannula and guard are pushed towards one another to engage the interior surface first zone of the central chamber of the guard with the hub of the hypodermic needle to secure the guard to the hypodermic needle cannula. If, by some chance, the combined guard and hypodermic needle cannula are hit or dropped, the probability that the tip of the cannula will exit the slot of the guard of the present invention is very low because of the labyrinth passage/screen wall and/or collapsed slot feature.

The present invention has been described with respect to a hypodermic needle cannula separable from the hypodermic needle and having its own hub. However, in many instances, the cannula is an integral part of the hypodermic needle and the cannula hub is the base of the hypodermic needle. The hub of the cannula for purposes of this invention means the hub of the cannula or the base of a hypodermic needle of which the cannula is an integral part. In those instances where the cannula and the hypodermic needle are an integral device, the guard will be sized to receive and secure the base of the hypodermic needle. In those instances where the hypodermic needle and the cannula are separate components and the cannula has its own hub, the guard will be sized such that the receiver end of the guard is adapted to secure the hub of the cannula. Although the invention has been described with respect to specific embodiments of the hypodermic needle cannula guard, the invention is not intended to be so limited, but the invention is intended to cover any guard which prevents the inadvertent exit or escape of the cannula from the guard via the guard's open slot or collapsed slot.

What is claimed is:

1. A guard for hypodermic needle cannula comprising: an elongated hollow shell having an interior wall, an exterior wall, an open receiver end and an opposing distal end, the shell having an interior central chamber extending the length of the shell from the open end bounded by the interior wall, the shell divided into a first zone extending longitudinally from the open receiver end and adapted to receive and secure the hub of the hypodermic needle cannula and a second zone extending from the first zone to the distal end and adapted to receive and enclose a hypodermic needle cannula, the shell having a slot running a substantial length of the shell from the open receiver end, the slot forming a passage from the exterior of the shell into the central chamber; and a screen wall having an L-shaped cross-section, one arm of the L extending radially inwardly from the interior wall of the shell proximate one side of the slot and a second arm of the screen wall extending circumferentially from the first arm, spaced apart, but across the slot, to screen the slot from the central chamber to inhibit the chance exit of a hypodermic needle cannula from the central chamber though the slot.

2. The guard according to claim 1 wherein the opposing distal end is at least partially enclosed with an screen wall.

3. The guard according to claim 1 wherein the screen wall is within the second zone of the shell.

4. The guard according to claim 3 wherein the longitudinal slot is an open slot of predetermined dimensions adapted to receive a hypodermic needle cannula.

5. The guard according to claim 4 wherein the open slot has a widened portion at the open receiver end to accommodate entry of a hypodermic needle cannula.

6. The guard according to claim 5 wherein the widened portion of the slot defines a V-shape.

7. The guard according to claim 1 wherein the screen wall extends the length of the second zone.

8. The guard according to claim 1 wherein the screen wall is discontinuous and comprises a plurality of screen walls extending the length of the shell in the second zone.

* * * * *